United States Patent
Mickus et al.

(10) Patent No.: US 11,707,264 B2
(45) Date of Patent: Jul. 25, 2023

(54) ROLLABLE TISSUE SPECIMEN BAG WITH IMPROVED BRIM FOR TENTING

(71) Applicant: Covidien LP, Mansfield, MA (US)

(72) Inventors: Jason Mickus, North Haven, CT (US); Jacob C. Baril, North Haven, CT (US); Saumya Banerjee, North Haven, CT (US)

(73) Assignee: Covidien LP, Mansfield, MA (US)

( * ) Notice: Subject to any disclaimer, the term of this patent is extended or adjusted under 35 U.S.C. 154(b) by 707 days.

(21) Appl. No.: 16/776,880

(22) Filed: Jan. 30, 2020

(65) Prior Publication Data

US 2021/0236103 A1     Aug. 5, 2021

(51) Int. Cl.
*A61B 17/00* (2006.01)

(52) U.S. Cl.
CPC ..... *A61B 17/00234* (2013.01); *A61B 2017/0042* (2013.01); *A61B 2017/00287* (2013.01); *A61B 2017/00831* (2013.01)

(58) Field of Classification Search
CPC .... A61B 17/00234; A61B 2017/00287; A61B 2017/0042; A61B 2017/00831; A61B 2017/00858
See application file for complete search history.

(56) References Cited

U.S. PATENT DOCUMENTS

| | | | |
|---|---|---|---|
| 5,480,404 A * | 1/1996 | Kammerer | A61B 17/00234 606/127 |
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |
| 6,358,198 B1 | 3/2002 | Levin et al. | |
| 6,368,328 B1 | 4/2002 | Chu et al. | |

(Continued)

*Primary Examiner* — Diane D Yabut
*Assistant Examiner* — Rachel S Highland
(74) *Attorney, Agent, or Firm* — Carter, DeLuca & Farrell LLP (57) ABSTRACT

A tissue specimen retrieval bag assembly includes a tissue specimen bag having an open proximal end and a closed distal end, the proximal end including a cuff defined therein and extending therearound. A flexible bag brim is disposed within the cuff and is transitionable between a first, collapsed configuration and a second, expanded configuration. The flexible bag brim includes a cross section configured to facilitate both furling the tissue specimen bag onto itself around the bag brim when the bag brim is disposed in the second, expanded configuration and securing the tissue specimen bag in a desired furled configuration. The flexible bag brim includes a plurality of scallops defined along an inner peripheral surface thereof configured to facilitate furling the tissue specimen bag onto itself.

20 Claims, 10 Drawing Sheets

(56) References Cited

U.S. PATENT DOCUMENTS

| | | | |
|---|---|---|---|
| 6,383,195 B1 | 5/2002 | Richard | |
| 6,383,197 B1 | 5/2002 | Conlon et al. | |
| 6,387,102 B2 | 5/2002 | Pagedas | |
| 6,406,440 B1 | 6/2002 | Stefanchik | |
| 6,409,733 B1 | 6/2002 | Conlon et al. | |
| 6,447,523 B1 | 9/2002 | Middleman et al. | |
| 6,450,983 B1* | 9/2002 | Rambo | A61B 17/3431 600/206 |
| 6,530,923 B1 | 3/2003 | Dubrul et al. | |
| 6,537,273 B1 | 3/2003 | Sosiak et al. | |
| 6,752,822 B2 | 6/2004 | Jespersen | |
| 6,805,699 B2 | 10/2004 | Shimm | |
| 6,951,533 B2 | 10/2005 | Foley | |
| 6,986,774 B2 | 1/2006 | Middleman et al. | |
| 7,037,275 B1 | 5/2006 | Marshall et al. | |
| 7,052,501 B2 | 5/2006 | McGuckin, Jr. | |
| 7,087,062 B2 | 8/2006 | Dhindsa | |
| 7,101,379 B2 | 9/2006 | Gregory, Jr. et al. | |
| 7,101,380 B2 | 9/2006 | Khachin et al. | |
| 7,112,172 B2 | 9/2006 | Orban, III et al. | |
| 7,115,125 B2 | 10/2006 | Nakao et al. | |
| 7,144,400 B2 | 12/2006 | Byrum et al. | |
| 7,169,154 B1 | 1/2007 | Que et al. | |
| 7,229,418 B2 | 6/2007 | Burbank et al. | |
| 7,285,126 B2 | 10/2007 | Sepetka et al. | |
| 7,316,692 B2 | 1/2008 | Huffmaster | |
| 7,357,801 B2 | 4/2008 | Burbank et al. | |
| 7,534,252 B2 | 5/2009 | Sepetka et al. | |
| 7,547,310 B2 | 6/2009 | Whitfield | |
| 7,615,013 B2 | 11/2009 | Clifford et al. | |
| 7,618,437 B2 | 11/2009 | Nakao | |
| 7,645,283 B2 | 1/2010 | Reynolds et al. | |
| 7,650,887 B2* | 1/2010 | Nguyen | A61B 17/3423 128/889 |
| 7,670,346 B2 | 3/2010 | Whitfield | |
| 7,678,118 B2 | 3/2010 | Bates et al. | |
| 7,722,626 B2 | 5/2010 | Middleman et al. | |
| 7,727,227 B2 | 6/2010 | Teague et al. | |
| 7,731,722 B2 | 6/2010 | Lavelle et al. | |
| 7,731,723 B2 | 6/2010 | Kear et al. | |
| 7,762,959 B2 | 7/2010 | Bilsbury | |
| 7,762,960 B2 | 7/2010 | Timberlake et al. | |
| 7,875,038 B2 | 1/2011 | Que et al. | |
| 7,892,242 B2 | 2/2011 | Goldstein | |
| 7,914,540 B2 | 3/2011 | Schwartz et al. | |
| 7,918,860 B2 | 4/2011 | Leslie et al. | |
| 7,955,292 B2 | 6/2011 | Leroy et al. | |
| 8,057,485 B2 | 11/2011 | Hollis et al. | |
| 8,075,567 B2 | 12/2011 | Taylor et al. | |
| 8,118,816 B2 | 2/2012 | Teague | |
| 8,152,820 B2 | 4/2012 | Mohamed et al. | |
| 8,172,772 B2 | 5/2012 | Zwolinski et al. | |
| 8,211,115 B2 | 7/2012 | Cheng et al. | |
| 8,282,572 B2 | 10/2012 | Bilsbury | |
| 8,337,510 B2 | 12/2012 | Rieber et al. | |
| 8,348,827 B2 | 1/2013 | Zwolinski | |
| 8,409,216 B2 | 4/2013 | Parihar et al. | |
| 8,414,596 B2 | 4/2013 | Parihar et al. | |
| 8,419,749 B2 | 4/2013 | Shelton, IV et al. | |
| 8,425,533 B2 | 4/2013 | Parihar et al. | |
| 8,430,826 B2 | 4/2013 | Uznanski et al. | |
| 8,435,237 B2 | 5/2013 | Bahney | |
| 8,444,655 B2 | 5/2013 | Parihar et al. | |
| 8,486,087 B2 | 7/2013 | Fleming | |
| 8,512,351 B2 | 8/2013 | Teague | |
| 8,579,914 B2 | 11/2013 | Menn et al. | |
| 8,585,712 B2 | 11/2013 | O'Prey et al. | |
| 8,591,521 B2 | 11/2013 | Cherry et al. | |
| 8,652,147 B2 | 2/2014 | Hart | |
| 8,721,658 B2 | 5/2014 | Kahle et al. | |
| 8,734,464 B2 | 5/2014 | Grover et al. | |
| 8,777,961 B2 | 7/2014 | Cabrera et al. | |
| 8,795,291 B2 | 8/2014 | Davis et al. | |
| 8,821,377 B2 | 9/2014 | Collins | |
| 8,827,968 B2 | 9/2014 | Taylor et al. | |
| 8,870,894 B2 | 10/2014 | Taylor et al. | |
| 8,906,035 B2 | 12/2014 | Zwolinski et al. | |
| 8,956,370 B2 | 2/2015 | Taylor et al. | |
| 8,968,329 B2 | 3/2015 | Cabrera | |
| 8,986,321 B2 | 3/2015 | Parihar et al. | |
| 9,005,215 B2 | 4/2015 | Grover et al. | |
| 9,017,328 B2 | 4/2015 | Bahney | |
| 9,017,340 B2 | 4/2015 | Davis | |
| 9,033,995 B2 | 5/2015 | Taylor et al. | |
| 9,084,588 B2 | 7/2015 | Farascioni | |
| 9,101,342 B2 | 8/2015 | Saleh | |
| 9,113,848 B2 | 8/2015 | Fleming et al. | |
| 9,113,849 B2 | 8/2015 | Davis | |
| 9,308,008 B2 | 4/2016 | Duncan et al. | |
| 9,364,201 B2 | 6/2016 | Drban, III | |
| 9,364,202 B2 | 6/2016 | Menn et al. | |
| 9,370,341 B2 | 6/2016 | Ceniccola et al. | |
| 9,370,378 B2 | 6/2016 | O'Prey et al. | |
| 9,375,224 B2 | 6/2016 | Jansen | |
| 9,414,817 B2 | 8/2016 | Taylor et al. | |
| 9,468,452 B2 | 10/2016 | Menn et al. | |
| 9,486,188 B2 | 11/2016 | Secrest et al. | |
| 9,522,034 B2 | 12/2016 | Johnson et al. | |
| 9,549,747 B2 | 1/2017 | Carlson | |
| 9,579,115 B2 | 2/2017 | Kahle et al. | |
| 9,592,067 B2 | 3/2017 | Hartoumbekis | |
| 9,622,730 B2 | 4/2017 | Farascioni | |
| 9,629,618 B2 | 4/2017 | Davis et al. | |
| 9,642,638 B1 | 5/2017 | Carrier | |
| 9,655,644 B2 | 5/2017 | Collins | |
| 9,730,716 B2 | 8/2017 | Secrest et al. | |
| 9,789,268 B2 | 10/2017 | Hart et al. | |
| 9,808,228 B2 | 11/2017 | Kondrup et al. | |
| 9,826,997 B2 | 11/2017 | Cherry et al. | |
| 9,867,600 B2 | 1/2018 | Parihar et al. | |
| 9,877,893 B2 | 1/2018 | Taylor et al. | |
| 2017/0325800 A1* | 11/2017 | Prior | A61B 17/00234 |

* cited by examiner

ROLLABLE TISSUE SPECIMEN BAG WITH IMPROVED BRIM FOR TENTING

BACKGROUND

Technical Field

The present disclosure relates to tissue specimen retrieval from an internal body cavity and, more particularly, to specimen retrieval or specimen containment bags that facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment such as a specimen retrieval bag or containment bag is highly desirable to inhibit seeding of cancer cells. Thus, with respect to breaking down large tissue specimens for retrieval through minimally-invasive openings, there is the added challenge of doing so within an enclosed environment.

In these instances, a standalone tissue bag may be utilized to contain large tissue specimens such as a uterus for hysterectomies or fibroids for myomectomies. The specimen retrieval bag or containment bag typically includes a bag brim having a flexible wire support that is transitionable between a first collapsed configuration for insertion through an incision or natural body orifice and a second expanded configuration for encapsulating tissue specimens. The bag brim, once externalized, may be manipulated or rolled to enhance surgical access to the tissue specimen or "tent" the specimen as needed.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

In accordance with aspects of the present disclosure is a tissue specimen retrieval bag assembly that includes a tissue specimen bag having an open proximal end and a closed distal end, the proximal end including a cuff defined therein and extending therearound. A flexible bag brim is disposed within the cuff and is transitionable between a first, collapsed configuration and a second, expanded configuration, the flexible bag brim including a cross section configured to facilitate both furling the tissue specimen bag onto itself around the bag brim when the bag brim is disposed in the second, expanded configuration and securing the tissue specimen bag in a desired furled configuration. The flexible bag brim includes a plurality of scallops defined along an inner peripheral surface thereof configured to facilitate furling the tissue specimen bag onto itself.

In aspects according to the present disclosure, at least one of the plurality of scallops includes at least one of a vent or a gate configured to facilitate manufacturing the flexible bag brim. In other aspects according to the present disclosure, the flexible bag brim includes a concave surface defined along an outer peripheral surface thereof. In still other aspects according to the present disclosure, the cross section includes a D-shaped cross section or a tri-lobular cross section. In yet other aspects according to the present disclosure, the cross section is tri-lobular and includes two or more edges that define a concave section therebetween configured to facilitate gripping the tissue specimen bag when furling.

In aspects according to the present disclosure, the tissue specimen bag is made from nylon and/or polyurethane.

In accordance with aspects of the present disclosure is a tissue specimen retrieval bag assembly that includes a tissue specimen retrieval bag assembly that includes a tissue specimen bag having an open proximal end and a closed distal end, the proximal end including a cuff defined therein and extending therearound. A flexible bag brim is disposed within the cuff and is transitionable between a first, collapsed configuration and a second, expanded configuration, the flexible bag brim including a cross section configured to facilitate both furling the tissue specimen bag onto itself around the bag brim when the bag brim is disposed in the second, expanded configuration and securing the tissue specimen bag in a desired furled configuration. The flexible bag brim includes a plurality of slots defined therethrough configured to facilitate handling of the flexible bag brim with a surgical instrument.

In aspects according to the present disclosure, the flexible bag brim includes a concave surface defined along an outer peripheral surface thereof. In other aspects according to the present disclosure, the cross section includes a tri-lobular cross section.

In aspects according to the present disclosure, the cross section is tri-lobular and includes at least two edges that define a concave section therebetween configured to facilitate gripping the tissue specimen bag when furling. In other aspects according to the present disclosure, the plurality of slots allows handling of the flexible bag brim by a medical instrument in a direction parallel to the flexible bag brim.

In accordance with aspects of the present disclosure is a tissue specimen retrieval bag assembly that includes a tissue specimen retrieval bag assembly that includes a tissue specimen bag having an open proximal end and a closed distal end, the proximal end including a cuff defined therein and extending therearound. A flexible bag brim is disposed within the cuff and is transitionable between a first, collapsed configuration and a second, expanded configuration, the flexible bag brim including a cross section configured to facilitate both furling the tissue specimen bag onto itself around the bag brim when the bag brim is disposed in the second, expanded configuration and securing the tissue specimen bag in a desired furled configuration. The flexible bag brim includes a rim disposed along an inner periphery thereof, the rim including a plurality of slots defined therethrough configured to facilitate handling of the flexible bag brim with a surgical instrument.

In aspects according to the present disclosure, the flexible bag brim includes a concave surface defined along an outer peripheral surface thereof. In other aspects according to the present disclosure, the cross section includes a tri-lobular cross section.

In aspects according to the present disclosure, the plurality of slots in the rim allows handling of the flexible bag brim by a medical instrument in a direction perpendicular to the flexible bag brim. In yet other aspects according to the present disclosure, the flexible bag brim includes a plurality of second slots defined therethrough configured to facilitate handling of the flexible bag brim with a surgical instrument in a direction parallel to the flexible bag brim.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
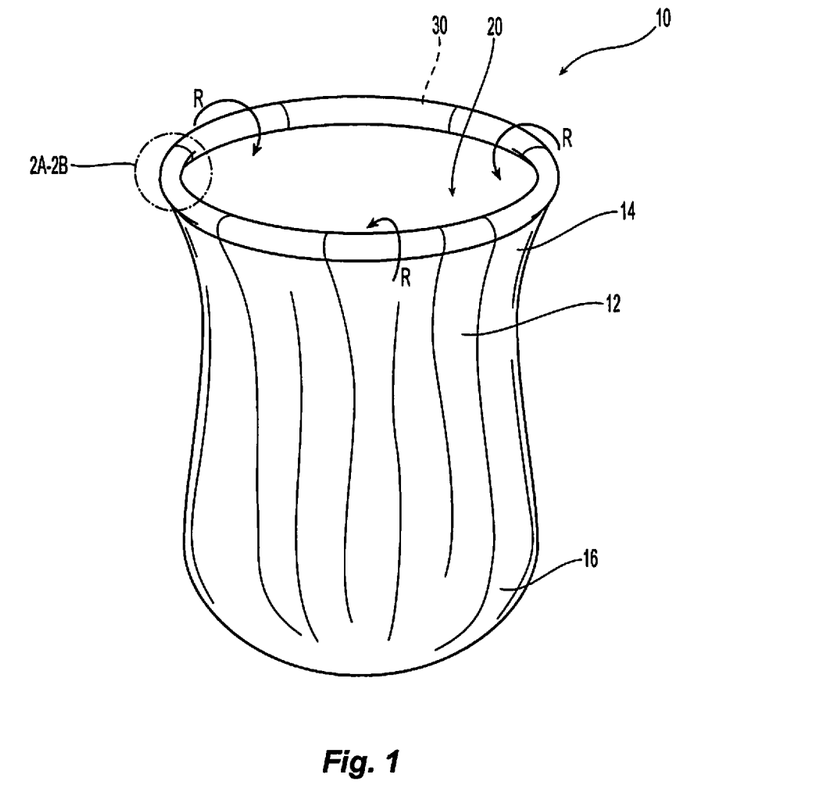
FIG. 1 is a perspective view of a tissue specimen bag provided in accordance with aspects of the present disclosure.
Figure 2A:
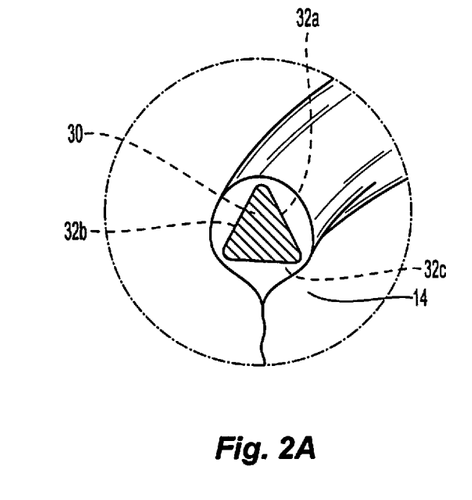
FIG. 2A is a cross sectional view of the area of detail of FIG. 1 showing one embodiment of a tri-lobular, rollable bag brim design.

Turning initially to FIGS. 1-2A, one embodiment of a standalone tissue specimen retrieval bag or tissue containment bag assembly is shown and is represent by reference numeral 10. Bag assembly 10 includes a bag 12 having a proximal end 14 including an opening 20 defined therein and an enclosed distal end 16. Bag assembly 10 includes bag rim 30 that is configured to support bag 12 in such a fashion as to define opening 20 when the bag 12 is unfurled or in an open configuration. Opening 20 is of sufficient dimension to receive one or more tissue specimens "T" during a particular surgical procedure.

Bag rim 30 is configured to be flexible such that the bag brim 30 is easily transitionable between a first, collapsed configuration wherein the bag 12 is furled (as explained below) and a second, expanded configuration which allows the bag 12 to be unfurled for receipt of a tissue specimen "T". As such, bag brim 30 may be made from any flexible material that is easily expandable from a collapsed configuration. Bag 12 may include any suitable rollable material such as nylon, polyurethane, etc.

Turning now to FIG. 2A, the bag brim 30 is configured to seat within an elongated cuff 18 defined in the proximal end of the bag 12. More particularly, bag brim 30 is of sufficient dimension to fit within the cuff 18 along an entire length thereof. Bag brim 30 may include two mating ends that, when engaged, form a generally circular configuration when opened to support bag 12 thereon. Bag brim 30 is generally triangular in shape and includes three sides 32a, 32b and 32c. Other geometric configurations or multi-sided arrangements are also envisioned and may be tailored for a particular purpose.

The generally triangular shape of the bag brim 30 allows the bag 12 to roll or furl around itself which, in turn, allows a surgeon to tent (i.e., position) the tissue specimen "T" closer to the proximal end of the operating cavity as needed for dissection. More particularly, the geometry of the sides 32a, 32b and 32c of the bag brim 30 facilitate furling/unfurling the bag 12 as needed and securing the bag 12 in a desired furled position.

In use, the specimen "T" is placed into the specimen bag 12 through opening 20. The weight of the specimen "T" causes the specimen "T" to fall to toward the distal end 16 of the bag 12. The proximal end 14 of the bag 12 and the circularly-shaped bag brim 30 maintain the proximal end 14 the bag 12 outside the operating cavity (See for example, FIG. 5C). If the surgeon desires to bring the specimen "T" closer to the proximal end 14 of the bag 12, the surgeon furls the bag 12 around the bag brim 30 in the direction "R". The triangular shape of the bag brim 30 facilitates furling the bag 12 and the brim 30 over on itself which, in turn, allows the surgeon to position the tissue specimen "T" at a desired depth "L" (See for example, FIG. 5B) within the surgical cavity depending upon a particular purpose. The sides 32a, 32b and 32c of the bag brim 30 may include a high friction surface to facilitate gripping the bag 12 when furling.

Figure 2B:
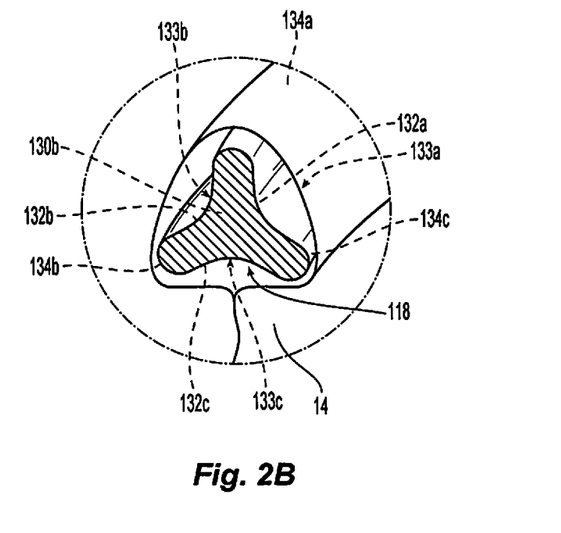
FIG. 2B is a cross sectional view of the area of detail of FIG. 1 showing another embodiment of a tri-lobular, rollable bag brim design.

FIG. 2B shows an alternative triangular-shaped bag brim 130 disposed within a cuff 118 having three generally rounded sides 132a, 132b and 132c separated by concave sections 133a, 133b and 133c., i.e., a tri-lobular-shaped cross section. The concave sections 133a, 133b and 133c allow the bag 12 to furl into a tighter configuration due to the geometry of the concave sections 133a, 133b and 133c. Moreover, each concave edge 134a, 134b and 134c of the bag brim 130 facilitates gripping the bag 12 during furling allowing a tighter and more secure furl. The concave edges 134a, 134b and 134c of the bag brim 130 may include a high friction surface to facilitate gripping the bag 12 when furling.

Figure 3A:
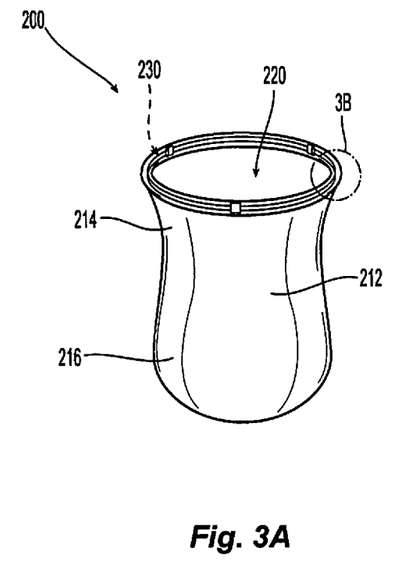
FIG. 3A is a perspective view of another embodiment of a tissue specimen retrieval bag having a flexible wire-like bag brim according to the present disclosure.
Figure 3B:
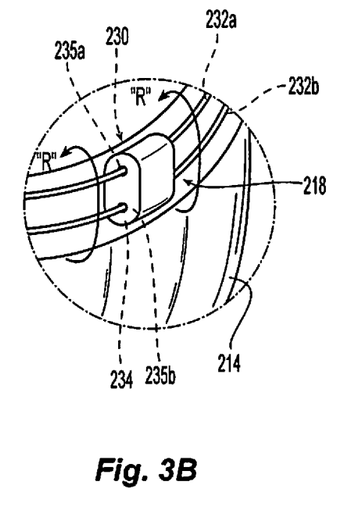
FIG. 3B is an enlarged view of the area of detail of FIG. 3A.

FIGS. 3A-3B show another embodiment of a tissue specimen retrieval bag assembly 200 for use with containing and supporting tissue specimens "T" within a surgical cavity. More particularly, bag assembly 200 includes a bag brim 230 having a bag 212 that depends therefrom for containing a tissue specimen "T". Bag brim 230 is disposed within a cuff 218 defined in a proximal end 214 of the bag 212. Bag brim 230 includes a pair of wires 232a, 232b that form the bag brim frame. A series of connectors or spacers 234 are spaced about the bag brim 230 and connect the two wires 232a, 232b together. More particularly, each connector 234 includes a pair of throughholes 235a, 235b defined therein that are each configured to receive a respective wire 232a, 232b of the bag brim 230. The number of connectors 234 depends on the type of wire 232a, 232b and the size of the bag brim 230. More connectors 234 will provide more consistent spacing along the bag brim 230.

In use and much like the embodiments shown in FIGS. 2A and 2B, a distal end 2116 of the bag 212 is placed within an operating cavity and a tissue specimen "T" is positioned through opening 220 of bag 212. The geometry of the bag brim 230 facilitates furling/unfurling the bag 212 as needed and secures the bag 212 in a desired furled position. More particularly, the shape of the bag brim 230 facilitates furling the bag 212 and the brim 230 in the direction of rotation "R" over on itself which, in turn, allows the surgeon to position the tissue specimen "T" at a desired depth "L" (See for example, FIG. 5B) within the surgical cavity depending upon a particular purpose.

Figure 3C:
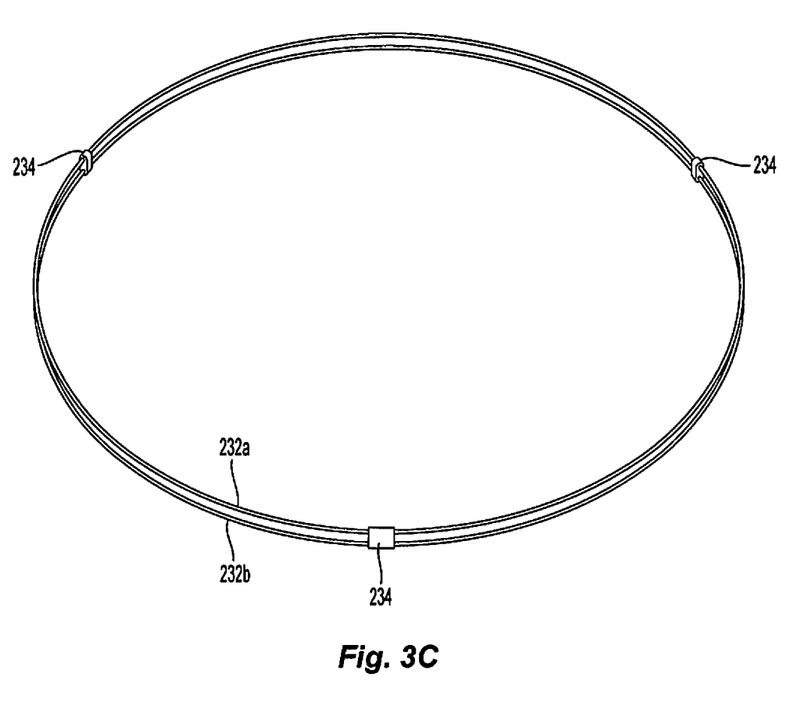
FIG. 3C is an enlarged view of the wire-like bag brim of FIG. 3A detached from the tissue specimen retrieval bag.

The wires 232a, 232b may be made of any know wire that is flexible such that the bag brim 230 is easily transitionable between a first collapsed configuration wherein the bag 212 is furled and a second expanded configuration which allows the bag 212 to be unfurled for receipt of a tissue specimen "T", e.g., a shape memory alloy (SMA) such as nickel-titanium alloy commonly sold under the tradename Nitinol® or copper-aluminum-nickel. Bag 212 may include any suitable rollable material such as nylon, polyurethane, etc.

Figure 4A:
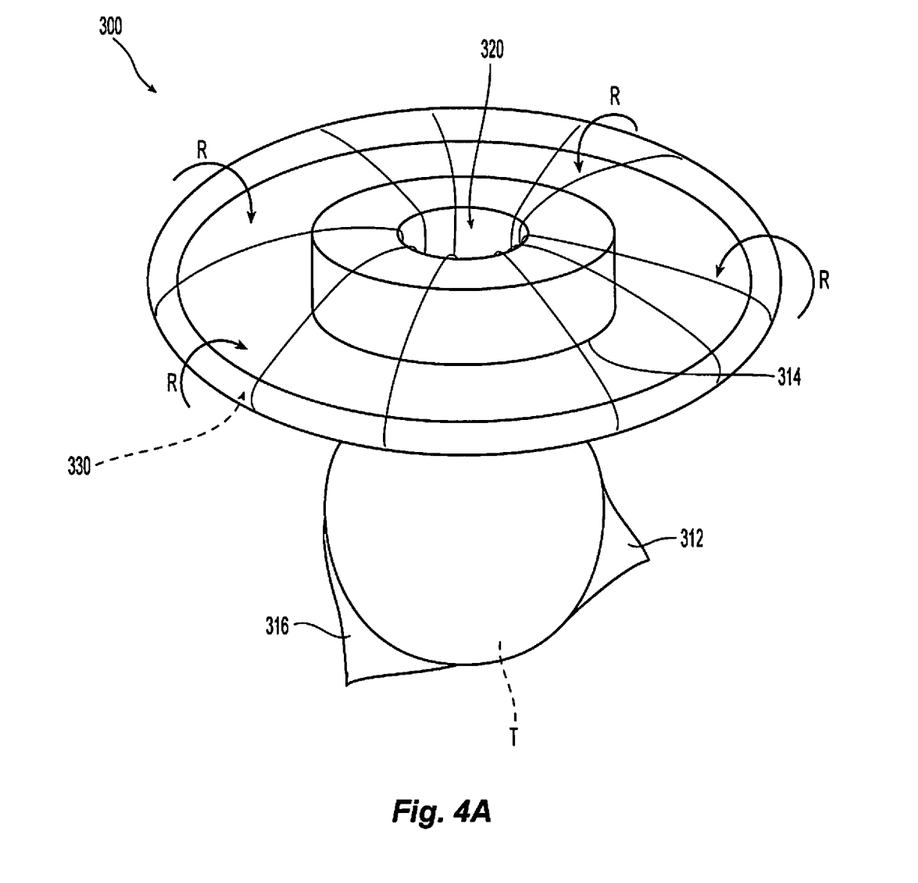
FIG. 4A is a perspective view of another embodiment of a tissue specimen retrieval bag having a rollable bag brim according to the present disclosure.
Figure 4B:
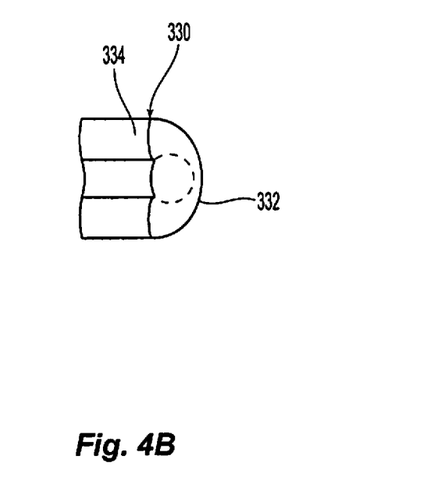
FIG. 4B is an enlarged, cross sectional view of the rollable bag brim of FIG. 4A.
Figure 5A:
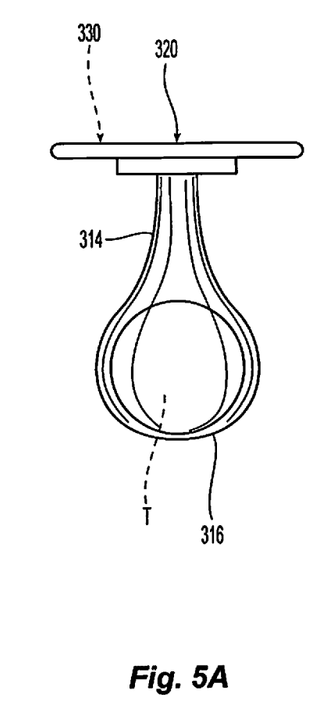
FIGS. 5A-5C are various views of the tissue specimen retrieval bag of FIGS. 4A and 4B for use with a tissue specimen "T"
Figure 5B:
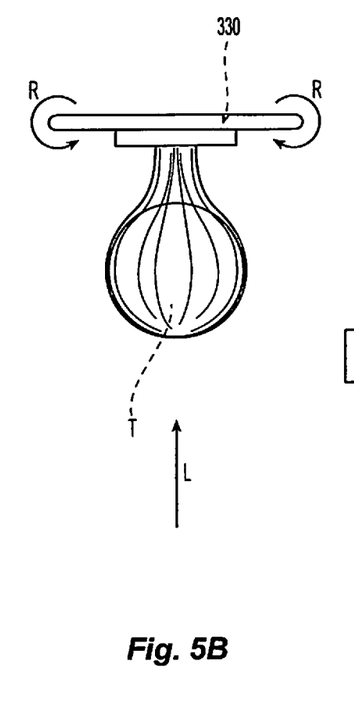
Figure 5C:
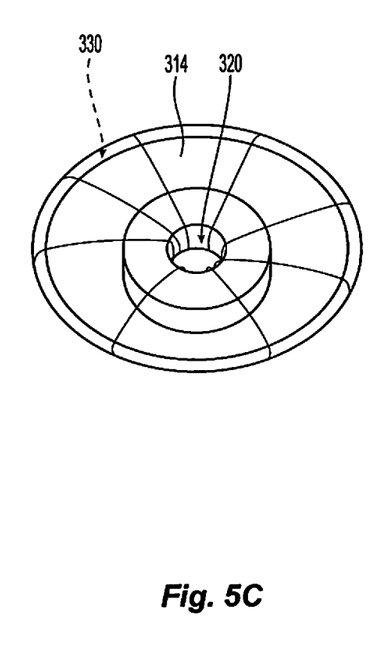

FIGS. 4-5C show another embodiment of a tissue specimen retrieval bag assembly 300 for use with containing and supporting tissue specimens "T" within a surgical cavity. More particularly, bag assembly 300 includes a bag brim 330 having a bag 312 that depends therefrom for containing a tissue specimen "T". Bag brim 330 is disposed within a cuff (not shown) defined in a proximal end 314 of the bag 312. Bag brim 330 is generally D-shaped and includes an arcuate side 332 and a generally flat side 334. Much like the embodiments shown above, the generally D-shaped bag brim 330 allows the bag 312 to roll or furl around itself which, in turn, allows a surgeon to tent (i.e., position) the tissue specimen "T" closer to the proximal end of the operating cavity as needed for dissection.

More particularly, and as best shown in FIGS. 5A-5C, the geometry of the sides 332, 334 of the bag brim 330 facilitate furling/unfurling the bag 312 as needed and securing the bag 312 in a desired furled position. As shown in FIG. 5A, the specimen "T" is place into the specimen bag 312 through opening 320. The weight of the specimen "T" causes the specimen "T" to fall to toward the distal end 316 of the bag 312. The proximal end 314 of the bag 312 and the circularly-shaped bag brim 330 maintain the proximal end 314 the bag 312 outside the operating cavity (See FIG. 5C). If the surgeon desires to bring the specimen "T" closer to the proximal end 314 of the bag 312, the surgeon furls the bag 312 around the bag brim 330 in the direction "R". The D-shape of the bag brim 330 facilitates furling the bag 312 and the brim 330 over on itself which, in turn, allows the surgeon to position the tissue specimen "T" at a desired depth "L" within the surgical cavity depending upon a particular purpose (See FIG. 5B). The flat side 334 and/or the arcuate side 332 may include a high friction surface to facilitate gripping the bag 312 when furling.

Figure 6A:
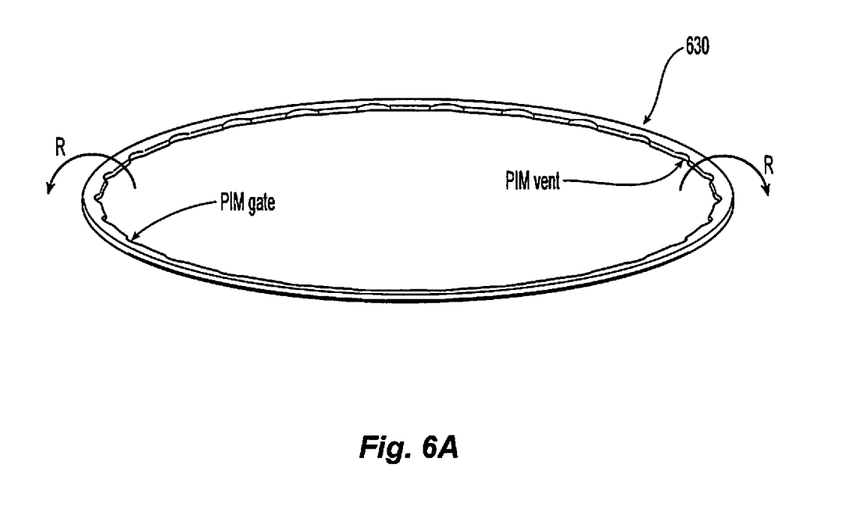
FIG. 6A is a perspective view of another embodiment of a rollable bag brim according another embodiment of the present disclosure.
Figure 6B:
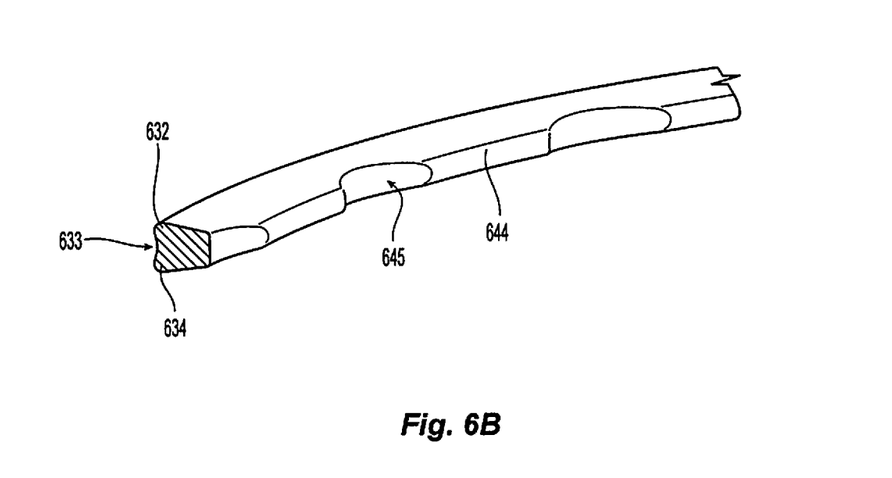
FIG. 6B is an enlarged, perspective view of the rollable bag brim of FIG. 6A.

FIGS. 6A and 6B show an alternate embodiment of a bag brim 630 for use with a tissue specimen retrieval bag 300. Bag brim 630 is generally circular-shaped much like the above-described bag brims. Bag brim 630 is configured to be flexible such that the bag brim 630 is easily transitionable between a first, collapsed configuration wherein the bag, e.g., bag 12, is furled (as explained above) and a second, expanded configuration which allows the bag 12 to be unfurled for receipt of a tissue specimen "T". As such, bag brim 630 may be made from any flexible material that is easily expandable from a collapsed configuration. Bag brim 630 may include a D-shaped cross section or may include a tri-lobular cross section (as explained in more detail below).

Bag brim 630 includes flexible upper and lower rims 632, 634, respectively, joined by a concave section 633 defined therebetween. Concave section 633 facilitates attachment of the bag 12 to the bag brim 630, e.g., via welding, gluing or melting thereon. A series of scallops 645 are defined along an inner peripheral surface 644 of the bag brim 630 and are configured to facilitate furling the bag 12 with minimal rotational force (e.g., force in the direction "R"). For example, the scallops 645 make furling the brim 630 easier due to the varying cross section of the bag brim 630 along the periphery 644 while at the same time maintaining the overall rigidity of the bag brim 630 for securing the bag 12 when tenting.

The scallops 645 may be "snapped off" or otherwise removed after molding. Moreover, as shown in FIG. 6A, the scallops 645 may allow good gating (PIM gate) and venting (PIM vent) locations during molding.

Figure 7A:
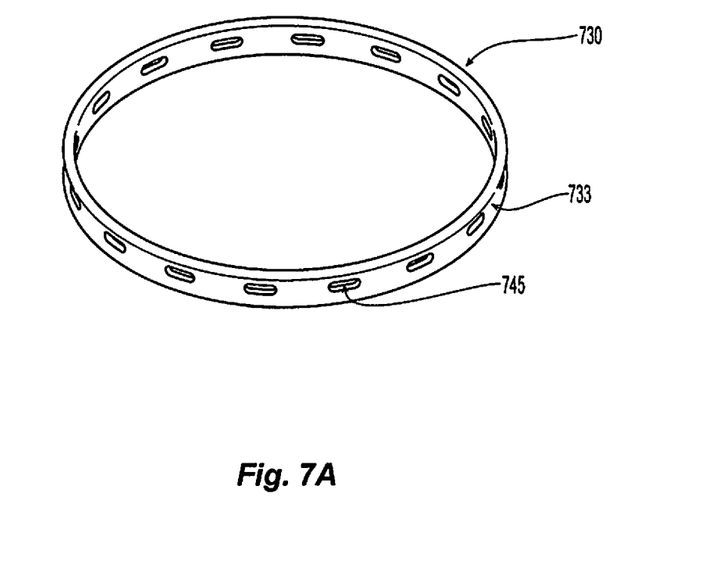
FIG. 7A is a perspective view of another embodiment of a rollable bag brim according another embodiment of the present disclosure.
Figure 7B:
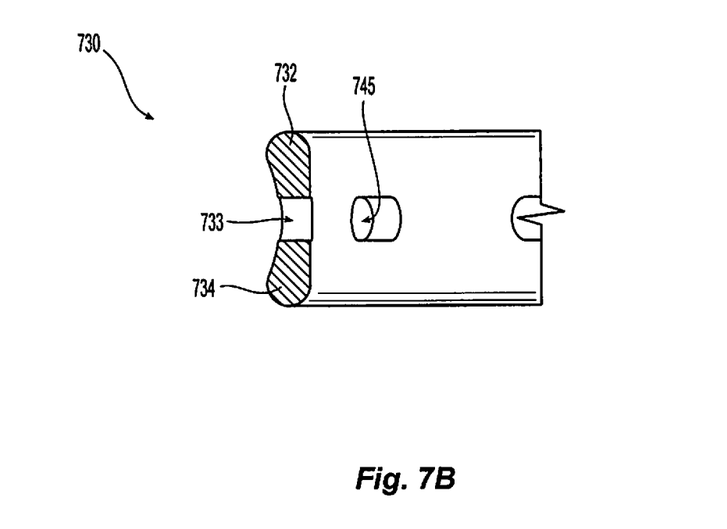
FIG. 7B is an enlarged, cross sectional view of the rollable bag brim of FIG. 7A.

FIGS. 7A and 7B show an alternate embodiment of a bag brim 730 for use with a tissue specimen retrieval bag 300. Bag brim 730 is generally circular-shaped and much like the above-described bag brims, bag brim 730 is configured to be flexible such that the bag brim 730 is easily transitionable between a first, collapsed configuration wherein the bag, e.g., bag 12, is furled (as explained above) and a second, expanded configuration which allows the bag 12 to be unfurled for receipt of a tissue specimen "T". As such, bag brim 730 may be made from any flexible material that is easily expandable from a collapsed configuration.

Bag brim 730 includes flexible upper and lower rims 732, 734, respectively, joined by a concave section 733 defined therebetween. Concave section 733 facilitates attachment of the bag 12 to the bag brim 730, e.g., via welding, gluing or melting thereon. Moreover, concave section 733 facilitates furling the bag 12 with minimal rotational force for tenting purposes.

Figure 7C:
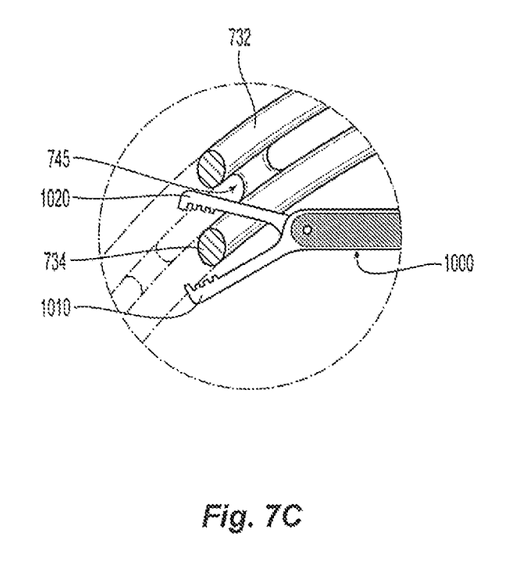
FIG. 7C is an enlarged, cross sectional view of the rollable bag brim of FIG. 7A illustrating manipulation thereof by a forceps.

A series of slots 745 are defined through the concave section 733 around the periphery of the bag brim 730 that facilitate grasping of the bag brim 730 therealong for manipulation purposes (see FIG. 7C.). More particularly, upper and lower jaw members 1010, 1020 of a forceps 1000 may easily grasp the bag bring 730 via engaging upper or lower rims 732, 734 of the bag brim 730 via slots 745. In this instance, a user is able to manipulate the bag brim 730 through the side thereof (in a coplanar or parallel direction).

Figure 8A:
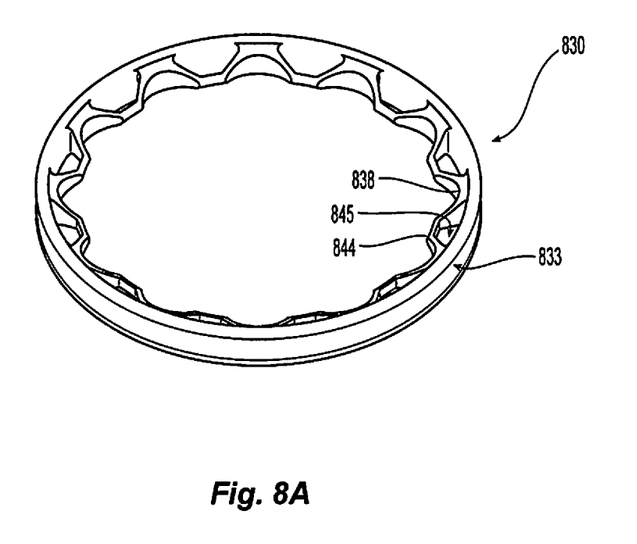
FIG. 8A is a perspective view of another embodiment of a rollable bag brim according another embodiment of the present disclosure.
Figure 8B:
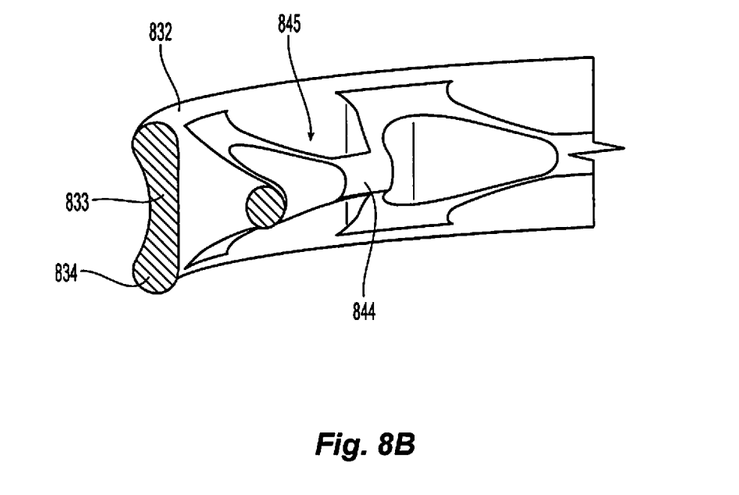
FIG. 8B is an enlarged, cross sectional view of the rollable bag brim of FIG. 8A.

FIGS. 8A and 8B show an alternate embodiment of a bag brim 830 for use with a tissue specimen retrieval bag 300. Bag brim 830 is generally circular-shaped and much like the above-described bag brims, bag brim 830 is configured to be flexible such that the bag brim 830 is easily transitionable between a first, collapsed configuration wherein the bag, e.g., bag 12, is furled (as explained above) and a second, expanded configuration which allows the bag 12 to be unfurled for receipt of a tissue specimen "T". As such, bag brim 830 may be made from any flexible material that is easily expandable from a collapsed configuration.

Bag brim 830 includes flexible upper and lower rims 832, 834, respectively, joined by a concave section 833 defined therebetween. Concave section 833 facilitates attachment of the bag 12 to the bag brim 830, e.g., via welding, gluing or melting thereon. Moreover, concave section 833 facilitates furling the bag 12 with minimal rotational force for tenting purposes.

A rim 844 extends along the inner periphery 838 of bag brim 830 and defines a series of slots 845 therein configured to allow manipulation of the bag brim 830 by forceps 1000. More particularly, upper and lower jaw members 1010, 1020 of a forceps 1000 may easily grasp the bag brim 830 via engaging rim 844 through slots 845. In this instance, a user is able to manipulate the bag brim 830 from the top or bottom thereof (e.g., in a direction normal to the bag brim 830).

Figure 9A:
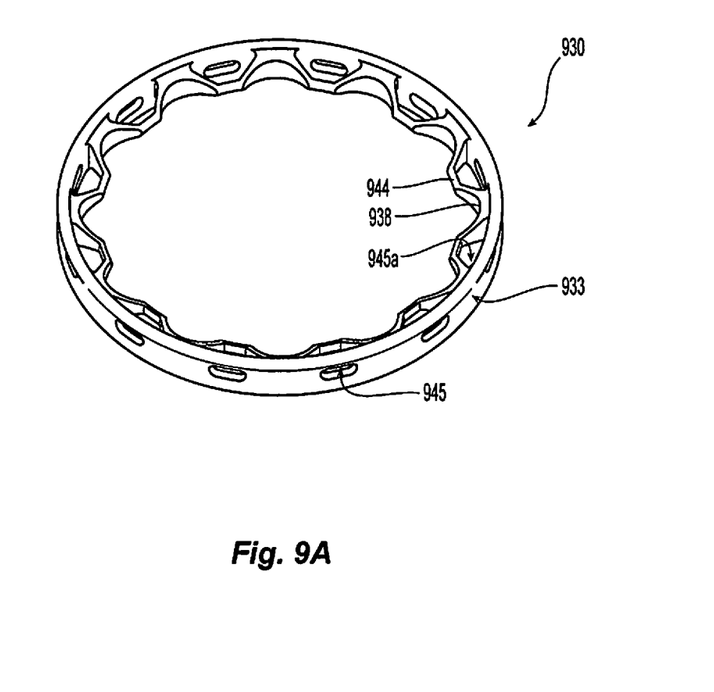
FIG. 9A is a perspective view of another embodiment of a rollable bag brim according another embodiment of the present disclosure.
Figure 9B:
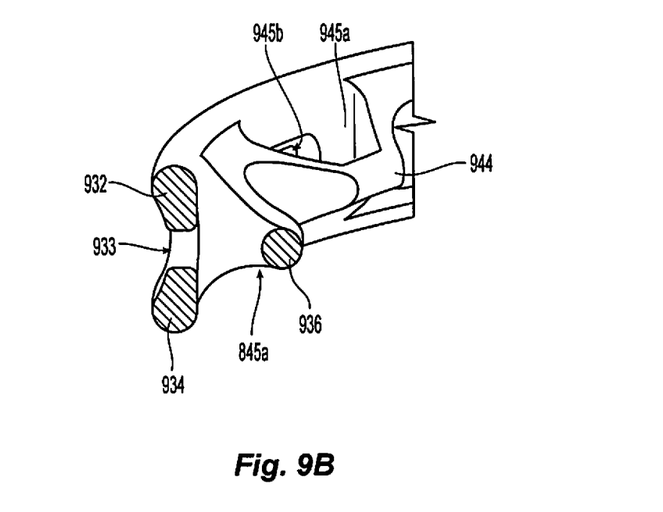
FIG. 9B is an enlarged, cross sectional view of the rollable bag brim of FIG. 9A.

FIGS. 9A and 9B show an alternate embodiment of a bag brim 930 for use with a tissue specimen retrieval bag 300. Bag brim 930 is essentially a combination of bag brim 730 and bag brim 830. More particularly, bag brim 930 is generally circular-shaped and much like the above-described bag brims, bag brim 930 is configured to be flexible such that the bag brim 930 is easily transitionable between a first, collapsed configuration wherein the bag, e.g., bag 12, is furled (as explained above) and a second, expanded configuration which allows the bag 12 to be unfurled for receipt of a tissue specimen "T". As such, bag brim 930 may be made from any flexible material that is easily expandable from a collapsed configuration.

Bag brim 930 includes flexible upper and lower rims 932, 934, respectively, joined by a concave section 933 defined therebetween. Concave section 933 facilitates attachment of the bag 12 to the bag brim 930, e.g., via welding, gluing or melting thereon. Moreover, concave section 933 facilitates furling the bag 12 with minimal rotational force for tenting purposes.

A rim 944 extends along the inner periphery 938 of bag brim 930 and defines a series of slots 945a therein configured to allow manipulation of the bag brim 930 by forceps 1000. More particularly, upper and lower jaw members 1010, 1020 of a forceps 1000 may easily grasp the bag brim 930 via engaging rim 944 through slots 945a. In this instance, a user is able to manipulate the bag brim 930 from the top or bottom thereof (e.g., in a direction normal to the bag brim 930).

A series of slots 945b are also defined through the concave section 933 around the periphery of the bag brim 930 and facilitate grasping of the bag brim 930 therealong for manipulation purposes. More particularly, upper and lower jaw members 1010, 1020 of forceps 1000 may easily grasp the bag bring 930 via engaging upper or lower rims 932, 934 of the bag brim 930 via slots 945b. In this instance, a user is able to also manipulate the bag brim 930 through the side thereof (in a coplanar or parallel direction).

Figure 9C:
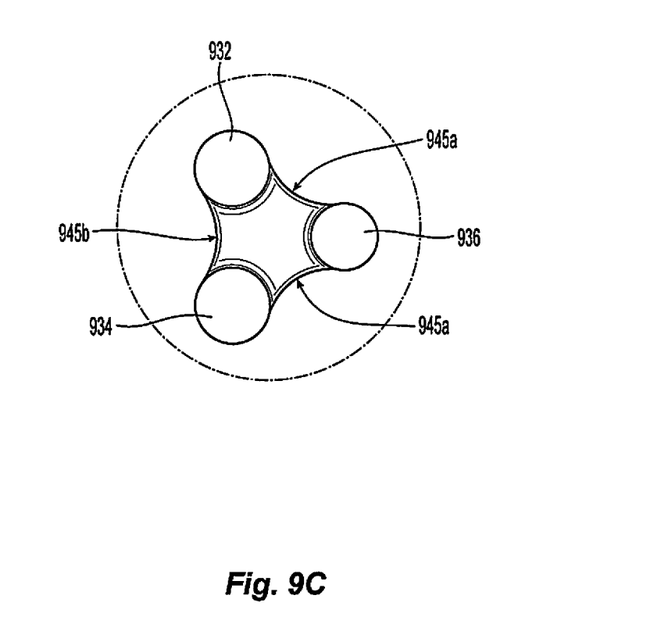
FIG. 9C is an enlarged, cross sectional view of the rollable bag brim of FIG. 9A illustrating a tri-lobular design for manipulation thereof by a forceps.

FIG. 9C shows a cross section of the bag brim 930 highlighting the tri-lobular profile. Essentially, the tri-lobular design of the bag brim 930 permits the forceps 1000 to grasp one of three sides 932, 934 and 936 of the bag brim through the top or side slots 945a, 945b.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval bag assembly, comprising:
   a tissue specimen bag having an open proximal end and a closed distal end, the tissue specimen bag including a cuff defined in, and extending around, the open proximal end; and
   a flexible bag brim disposed within the cuff, the flexible bag brim transitionable between a first, collapsed configuration and a second, expanded configuration, the flexible bag brim including a cross section configured to facilitate both furling the tissue specimen bag onto itself around the bag brim when the bag brim is disposed in the second, expanded configuration and securing the tissue specimen bag in a desired furled configuration, the flexible bag brim including an inner periphery, an outer periphery, and a rim disposed inwardly of the inner periphery, the flexible bag brim including a plurality of first slots defined through the rim and a plurality of second slots defined through the inner periphery and the outer periphery, the plurality of first slots and the plurality of second slots configured to facilitate handling of the flexible bag brim with a surgical instrument.

2. The tissue specimen retrieval bag assembly according to claim 1, wherein a concave surface is defined along an outer peripheral surface of the flexible bag brim.

3. The tissue specimen retrieval bag assembly according to claim 1, wherein the cross section includes a tri-lobular cross section.

4. The tissue specimen retrieval bag assembly according to claim 1, wherein the plurality of first slots in the rim allows handling of the flexible bag brim by the surgical instrument in a direction perpendicular to the flexible bag brim.

5. The tissue specimen retrieval bag assembly according to claim 1, wherein the plurality of second slots allows handling of the flexible bag brim by the surgical instrument in a direction parallel to the flexible bag brim.

6. The tissue specimen retrieval bag assembly according to claim 1, wherein the plurality of second slots is oriented substantially transverse to the plurality of first slots.

7. The tissue specimen retrieval bag assembly according to claim 1, wherein the cuff extends continuously around the open proximal end, and the flexible bag brim is circular.

8. The tissue specimen retrieval bag assembly according to claim 1, wherein the cuff is attached to the flexible bag brim at the outer periphery of the flexible bag brim.

9. The tissue specimen retrieval bag assembly according to claim 1, wherein the tissue specimen bag is made from at least one of nylon or polyurethane.

10. The tissue specimen retrieval bag assembly according to claim 1, wherein the flexible bag brim includes a series of scallops defined along an inner surface of the rim.

11. The tissue specimen retrieval bag assembly according to claim 1, wherein the plurality of first slots are disposed in radially spaced relation relative to each other around the flexible bag brim.

12. The tissue specimen retrieval bag assembly according to claim 1, wherein the plurality of second slots are disposed in radially spaced relation relative to each other around the flexible bag brim.

13. The tissue specimen retrieval bag assembly according to claim 1, wherein each of the plurality of second slots is in open communication with one of the plurality of first slots.

14. A tissue specimen retrieval bag assembly, comprising:
 a tissue specimen bag having an open proximal end and a closed distal end, the tissue specimen bag including a cuff defined in the open proximal end; and
 a flexible bag brim disposed within the cuff of the tissue specimen bag, the flexible bag brim transitionable between a collapsed configuration and an expanded configuration, the flexible bag brim including a cross section configured to facilitate both furling the tissue specimen bag onto itself around the bag brim when the bag brim is disposed in the expanded configuration and securing the tissue specimen bag in a desired furled configuration, the flexible bag brim including an inner periphery, an outer periphery, and a rim extending inwardly from the inner periphery, the flexible bag brim including a plurality of first slots defined through the rim and a plurality of second slots defined through the inner periphery and the outer periphery, the plurality of first slots oriented substantially transverse to the plurality of second slots.

15. The tissue specimen retrieval bag assembly according to claim 14, wherein the outer periphery of the flexible bag brim is concave.

16. The tissue specimen retrieval bag assembly of claim 15, wherein the tissue specimen bag is attached to flexible bag brim at the outer periphery of the flexible bag brim.

17. The tissue specimen retrieval bag assembly according to claim 14, wherein the cross section of the flexible bag brim is tri-lobular.

18. The tissue specimen retrieval bag assembly according to claim 14, wherein the plurality of first slots and the plurality of second slots are configured for handling of the flexible bag brim by a surgical instrument in different orientations relative to the flexible bag brim.

19. The tissue specimen retrieval bag assembly according to claim 14, wherein a portion of the flexible bag brim defined between the inner periphery and the outer periphery includes an upper rim and a lower rim joined by a concave section.

20. The tissue specimen retrieval bag assembly according to claim 19, wherein the plurality of second slots extends through the concave section of the flexible bag brim.

* * * * *